United States Patent [19]

Ransberger et al.

[11] Patent Number: 5,223,406
[45] Date of Patent: Jun. 29, 1993

[54] PROCESS OF USING CATABOLIC ENZYMES FOR INDUCTION OF TUMOR NECROSIS FACTOR (TNF)

[75] Inventors: Karl Ransberger, Grünwald; Gerhard Stauder, Wolfratshausen, both of Fed. Rep. of Germany

[73] Assignee: Mucos Emulsiongesellschaft m.b.H., Berlin, Fed. Rep. of Germany

[21] Appl. No.: 593,129

[22] Filed: Oct. 5, 1990

[30] Foreign Application Priority Data

Oct. 6, 1989 [EP] European Pat. Off. ....... 8911862810

[51] Int. Cl.⁵ .................. C12P 21/00; A61K 37/62; A61K 37/54; A61K 37/12
[52] U.S. Cl. ................... 435/68.1; 530/357; 424/94.2; 424/94.6
[58] Field of Search ............. 435/68.1; 530/357

[56] References Cited

U.S. PATENT DOCUMENTS 5,002,766 3/1991 Ransberger et al. ............ 424/94.2

OTHER PUBLICATIONS

Desser et al. (1990) *Oncology*, 47(6) 475–477, in *Chem Abstract* 115, 670, Abst #6663.
Riipi et al, (1990) *Infect. Immun.*, 58(9) 2750–2754, in *Biol. Abstract* 90(10), 475, Abst. #111308.
Zhang et al. (1990) *Acta Pharmacol. Sin.*, 11(4) 375–377, in *Biol. Abstr.*, 90(8), 730, Abstr #89125.
Ferrante et al. (1990) *Infect. Immun.*, 58(12), 3996–4003, in *Biol. Abstr.*, 91(4), 489, Abstr #39221.
Hajto et al. (1990) *Cancer Res.*, 50(11), 3322–3326.
Lefkowitz et al. (1990) *Life Sci.*, 47(8), 703–709.

Primary Examiner—Douglas W. Robinson
Assistant Examiner—Jon P. Weber
Attorney, Agent, or Firm—Reed Smith Shaw & McClay

[57] ABSTRACT

Methods for induction of the tumor necrosis factor, TNF, with at least one of the catabolic enzymes pancreatin, bromelain, papain, lipase, amylase, trypsin, and chymotrypsin are provided.

9 Claims, 7 Drawing Sheets

PROCESS OF USING CATABOLIC ENZYMES FOR INDUCTION OF TUMOR NECROSIS FACTOR (TNF)

DESCRIPTION

The present invention relates to the use of the enzymes pancreatin, bromelain, papain, lipase, amylase, trypsin and/or chymotrypsin for induction of the tumour necrosis factor (TNF).

The tumour necrosis factor is a glycoprotein produced within the body and formed in the monocyte system of MG 17,000 (human being) to 150,000 (mouse). The tumour necrosis factor was originally isolated as a protein which is capable of selectively killing tumour cells in vitro and in vivo. This ability of selectively attacking cancer cells without damaging healthy cells underscores the special interest in TNF as a therapeutic anticancer agent.

In addition to this, TNF has proved in the meantime to be a central immunomodulator, which can act, among other things, as a growth factor in fibroblasts, as an activator in the neutrophilic granulocytes and as an inhibitor in the differentiation of marrow cell lymphocytes. The tumour necrosis factor is induced by immunomodulators such as Interleukin-2. Interleukin-2 is isolated either from T-cells in an expensive process or synthetized by means of genetic engineering methods.

The present invention is based on the object of making an effective TNF inductive agent available, which can be produced at low cost.

According to the invention this object is accomplished by using at least one of the enzymes pancreatin, bromelain, pepain, lipase, amylase, trypsin and/or chymotrypsin for induction of the tumour necrosis factor (TNF).

It turned out surprisingly that the enzymes pancreatin, bromelain, papain, lipase, amylase, trypsin and/or chymotrypsin can stimulate the synthesis of the tumour necrosis factor in vitro and in vivo.

The enzymes used according to the invention can be isolated at low cost from the following raw materials.

Pancreatin is obtained from pig or bovine pancreas. It is commercially available as Kreon Granulat (Kali-Chemie) and Panzynorm (Nordmark)—Nordmark Arzneimittel.

Bromelain is a proteolytically active enzyme from the squeezed juice of pineapple. It is commercially available as Ananase—Traumanase Dragee (Rorer)—Taiwan McKay Biochem. Co. Ltd.

Figure 1A:
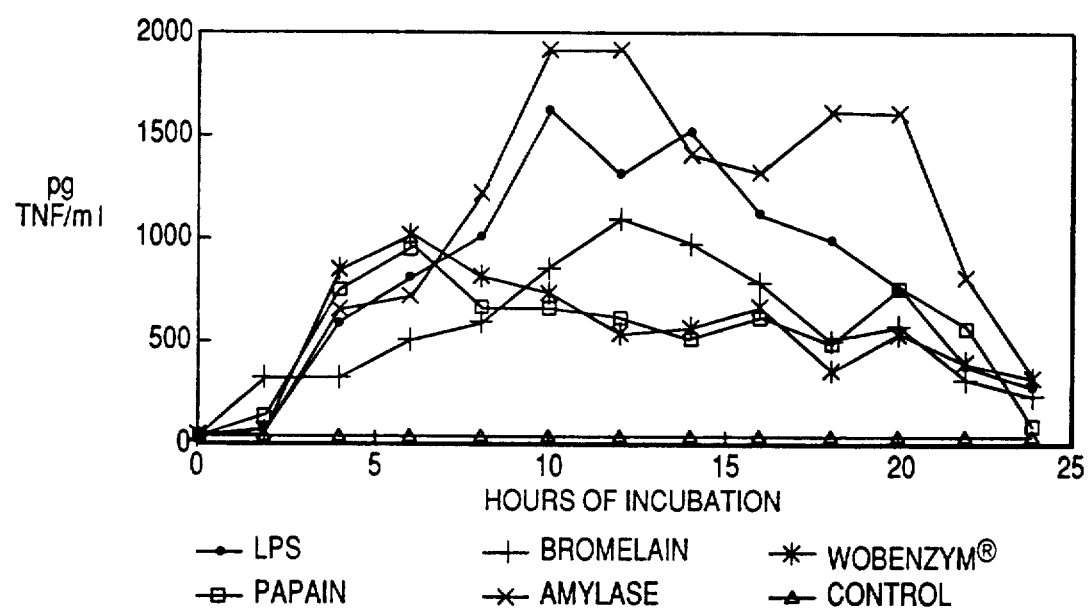
FIG. 1a is a graph showing the amount of TNF synthesized in mononuclear blood cells upon incubation with LPS (lipopolysaccharide), papain, bromelain, amylase, Wobenzym ®, and a control over a 24 hour period.
Figure 1B:
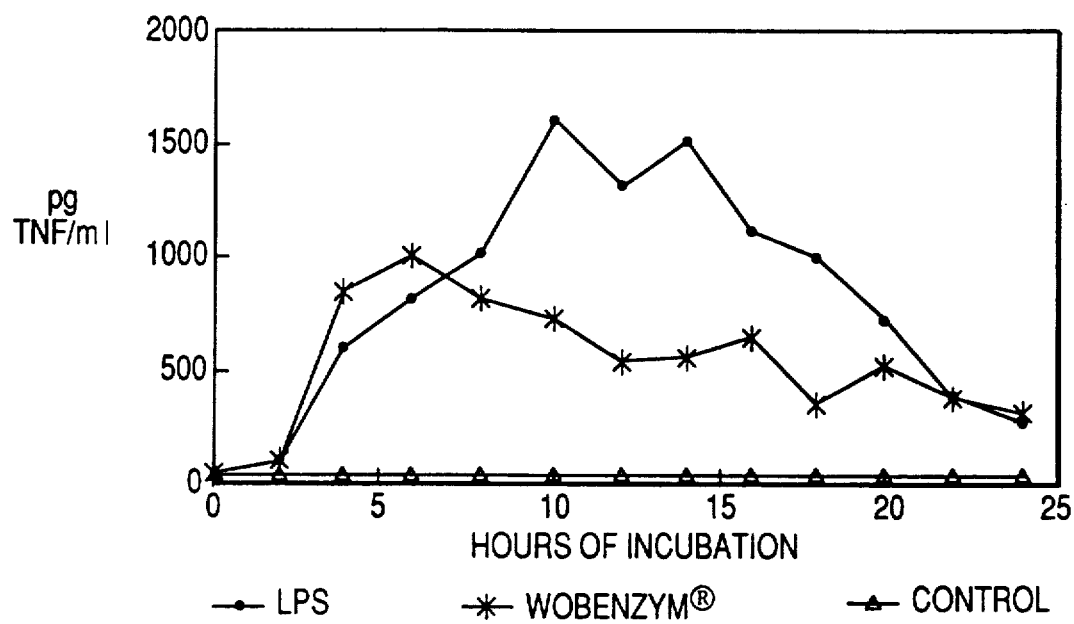
FIG. 1b is a graph showing the amount of TNF synthesized in mononuclear blood cells upon incubation with LPS, Wobenzym ®, and a control over a 24 hour period.
Figure 1C:
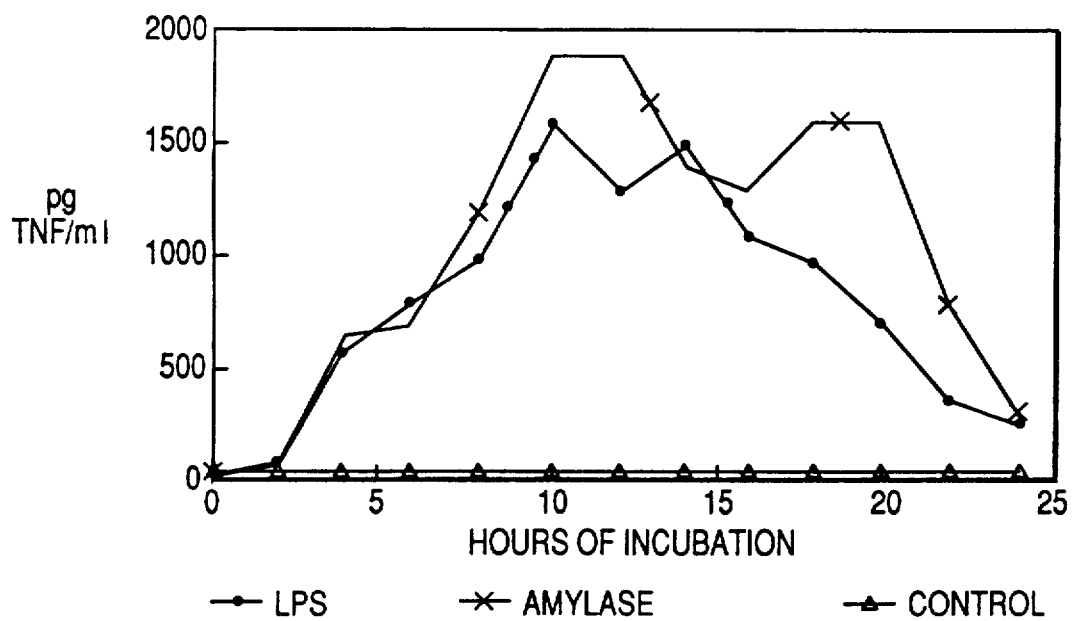
FIG. 1c is a graph showing the amount of TNF synthesized in mononuclear blood cells upon incubation with LPS, amylase, and a control over a 24 hour period.
Figure 1D:
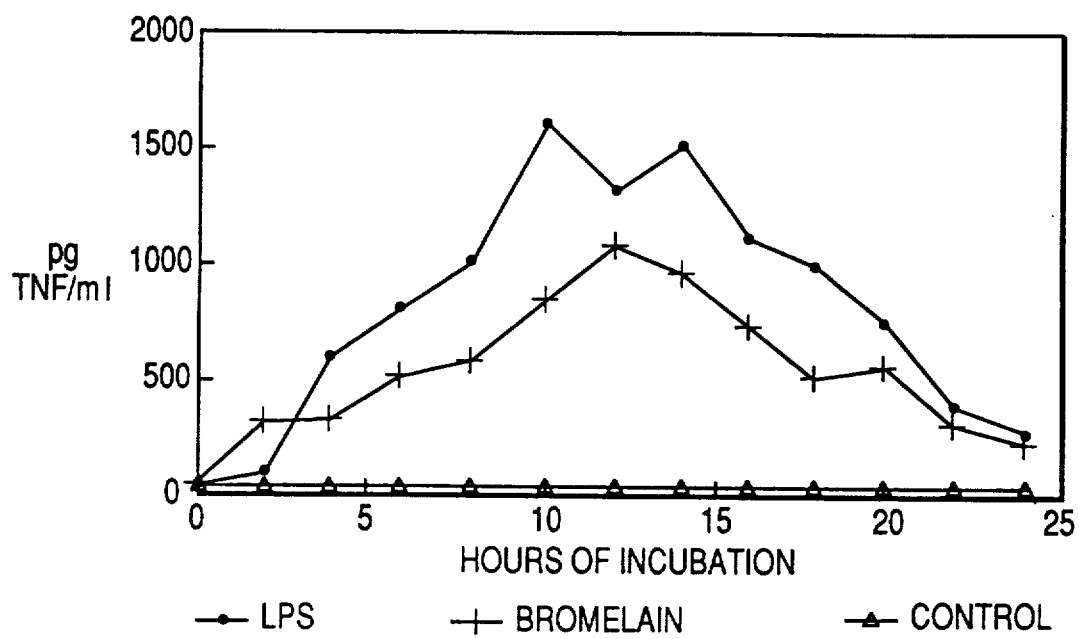
FIG. 1d is a graph showing the amount of TNF synthesized in mononuclear blood cells upon incubation with LPS, bromelain, and a control over a 24 hour period.
Figure 1E:
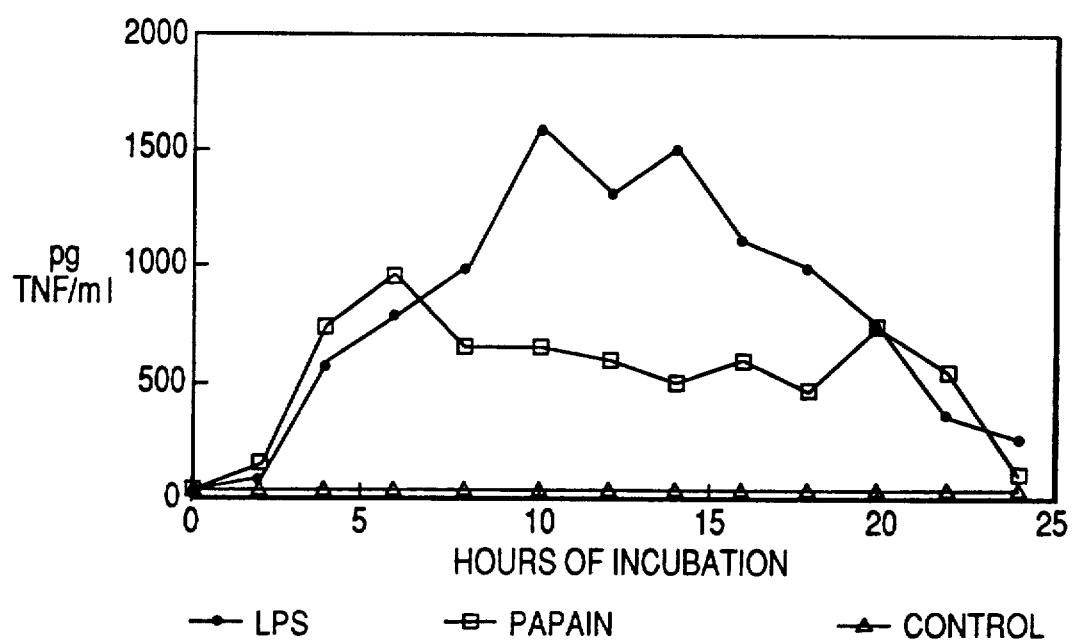
FIG. 1e is a graph showing the amount of TNF synthesized in mononuclear blood cells upon incubation with LPS, papain, and a control over a 24 hour period.

Papain is a proteolytic enzyme which is obtained from the chyle of the unripe, fleshy fruits of the Carica papoya melon tree. It is commercially available as Tonsilase (Pejo)—Biocon India Pvt. Ltd.

Lipases form part of the sub-group of the esterases and are obtained from pancreas or the Rhizophuus arrhizus fungus. They are commercially available from Ammano (Int. Enzyme Co., Inc.).

Amylases are glycoside-splitting enzymes which are, for instance, isolated from pancreas or special microorganisms. They are commercially available as Maxilase Tabletten (Sanofi)—Ammano Int. Enzyme Co., Inc.

Trypsin is a proteolytic enzymes which is also formed in the pancreas and has already been used therapeutically in connection with other enzymes. It is commercially available as Trypure (Novo)—Novo Industri A/S.

Chymotrypsin is a proteolytic enzymes which is also formed in the pancreas and has already been used therapeutically in connection with other enzymes. It is commercially available as Alfaquimotripsina Tabl. (Choay)—Biobras Bioquin. do Brasil S.A.

Triacyl glycerol lipase is preferably used as lipase and/or α-amylase is preferably used as amylase. They have a good effect as TNF inductive agent.

A special effectiveness becomes apparent if a combination of the enzymes pancreatin, bromelain, papain, triacyl glycerol lipase, α-amylase, trypsin and/or chymotrypsin are used. In addition to the remarkable and unexpected effect of these enzymes on TNF induction, the combined use of the mentioned enzymes has furthermore the advantage that no damaging secondary effects occur even in the case of a long-term application.

Rutoside or Rutin, a glycoside belonging to the flavonoids can additionally be used with preference. It is commercially available as Solvosal Dragee (Promonta) and Beniosan Dragee (Luitpold)—Merck do Brasil.

The combined use of 50 to 200 mg, preferably 100 mg, of pancreatin, 20 to 100 mg, preferably 45 mg, of bromelain, 40 to 100 mg, preferably 60 mg of papain, 5 to 50 mg, preferably 10 mg, of triacyl glycerol lipase, 5 to 509 mg, preferably 10 mg, of amylase, 10 to 30 mg, preferably 24 mg, of trypsin, 1 to 10 mg, preferably 1 mg, of chymotrypsin and 10 to 100 mg, preferably 50 mg, of rutoside ×3H$_2$O per dose unit has especially good effectiveness.

The preparation to be used may furthermore additionally contain Serratia peptidase. Serratia peptidse can be obtained from a microorganism of the Serratia species by standard procedures well known in the art.

The preparation to be used may furthermore contain customary adjuvants and/or carrier substances. Examples are disintegration agents, for example, starches such as corn starch or potato starch, polymers such as polyvinyl pyrrolidone, binders such as stearic acid and derivatives thereof, separating agents such as talcum kaoline, and fillers such as lactose. Additionally if the enzyme composition is provided in table form a stomach juice resistant coating may be provided, for example, one consisting of a methacrylate polymer or shellac.

The examples explain the invention.

EXAMPLE 1

The mononuclear cells (PMNC) were isolated from the heparinized blood of healthy donors via lymphopreparation. The separation into adherent (adh) and non-adherent (non-adh.) cells was effected in Petri dishes pretreated with FKS fetal calf serum with an incubation time of 1.5 to 4 hours. These cells were subsequently brought on microtiter plates with 96 wells (Costar) in a concentration of 5×10$^5$/ml and incubated with Wobenzym solution or its components for 20 hours (10 µg enzyme/ml).

The supernatants were removed, combined and frozen at −20° C. until their use. The percentage cytotoxicity of the supernatants of enzyme-treated cells was determined as compared with liposaccharide-activated cells by means of the tumour cell line L929 (see TNF determination).

The results are summarized in Table 1.

TABLE 1

Cytotoxicity (in %) of the supernatants of enzyme-treated, peripheral, mononuclear cells (adherent and non-adherent) as compared with lipopolysaccharide-activated cells

| Test | Cells | 0 | Wo[1] | Am[2] | Br[3] | Ch[4] | Li[5] | Pan[6] | Pap[7] | Tr[8] | LPS[10] |
|---|---|---|---|---|---|---|---|---|---|---|---|
| 51/56 | adh.[9] | 0 | 35 | 44 | 9 | 13 | 8 | 16 | 20 | 30 | 41 |
| 55/57 | adh. | 0 | 17 | 26 | 28 | 8 | 24 | 0 | 0 | 13 | 46 |
| 63/65 | adh. | 0 | 16 | 17 | 18 | 23 | 6 | 0 | 16 | 8 | 40 |
| 67/68 | adh. | 0 | 0 | 41 | 47 | 0 | 0 | 0 | 15 | 81 | 80 |
| 41/43 | adh. | 0 | 29 | 34 | 26 | 2 | 0 | 2 | 18 | 26 | 34 |
| 47/52 | adh. | 0 | 16 | 18 | n.d. | 8 | n.d. | n.d. | n.d. | n.d. | 36 |
| 63/65 | non adh. | 0 | 43 | 59 | 21 | 42 | 29 | 0 | 52 | 52 | 75 |
| 67/68 | non adh. | 0 | 18 | 47 | 39 | 0 | 23 | 0 | 9 | 50 | 82 |
| 67/68 | PMNC[11] | 0 | 19 | 50 | 70 | 0 | 0 | 0 | 65 | 0 | 81 |

[1]Wobenzym ®
[2]amylase
[3]bromelain
[4]chymotrypsin
[5]lipase
[6]pancreatin
[7]papain
[8]trypsin
[9]adherent cells
[10]lipopolysaccharide
[11]peripheral mononuclear cells In order to detect TNF in supernatants of the cell suspensions, the cytotoxicity was examined in the presence of human anti-TNF o in various dilutions. Peripheral, mononuclear cells or only adherent cells in a concentration of 5×10$^5$/ml microtiter plates with 96 wells were incubated for this purpose together with PHA (1 µg/ml), LPS (10 µg/ml) or the enzymes Wobenzym ®, amylase, bromelain, pancreatin, chymotrypsin or papain at 37° C. for 24 hours. The supernatants of the cell suspensions were transferred to microtiter plates with 96 wells, into whose wells L929 cells had been previously inserted. In addition to an actinomycin D solution (10 µg/ml), human anti-TNF in various dilutions was added.

The percentage cytotoxicity was determined 20 hours later by means of colouring of the living L 929 cells with crystal violet (see TNF determination). The results are represented in Tables 2a, b and c.

TABLE 2a

| Pretreatment of adherent cells | Cytotoxicity (in %) Dilution anti-TNF alpha | | | | |
|---|---|---|---|---|---|
| | 0 | 1:10000 | 1:1000 | 1:500 | 1:100 |
| PHA 1 µg/ml | 73 | nd | 47 | nd | 22 |
| PHA 1 µg/ml | 58 | nd | 15 | nd | 5 |
| LPS 10 µg/ml | 55 | nd | 40 | nd | 0 |
| LPS 10 µg/ml | 46 | nd | 0 | nd | 0 |
| LPS 10 µg/ml | 61 | nd | 0 | nd | 0 |
| TNF 1000 pg/ml | 74 | 66 | 39 | 34 | 33 |
| TNF 500 pg/ml | 70 | 38 | 24 | 33 | 33 |
| TNF 250 pg/ml | 62 | 26 | 20 | 0 | 0 |
| TNF 125 pg/ml | 49 | 14 | 0 | 0 | 0 |

TABLE 2b

| Pretreatment of adherent cells | Cytotoxicity (in %) Dilution anti-TNF alpha | | |
|---|---|---|---|
| | 0 | 1:1000 | 1:100 |
| Wobenzym 10 µg/ml ® | 50 | 22 | 0 |
| Wobenzym 10 µg/ml ® | 32 | 13 | 0 |
| Amylase 10 µg/ml | 29 | 8 | 0 |
| Papain 40 µg/ml | 58 | 30 | 8 |
| Papain 20 µg/ml | 60 | 52 | 16 |
| Papain 5 µg/ml | 42 | 24 | 0 |
| Papain 1 µg/ml | 33 | 0 | 0 |

TABLE 2c

Cytotoxicity (in %)
Dilution anti-TNF alpha

| Pretreatment of PMNC | 0 | 1:800 | 1:200 |
|---|---|---|---|
| Wobenzym ® | 80 | 15 | 0 |
| Amylase | 40 | 7 | 7 |
| Bromelain | 48 | 0 | 0 |
| Chymotrypsin | 19 | 7 | 0 |
| Lipase | 18 | 0 | 0 |
| Pancreatin | 22 | 8 | 0 |

TABLE 2c-continued

| | Cytotoxicity (in %) | | |
|---|---|---|---|
| | | Dilution anti-TNF alpha | |
| Pretreatment of PMNC | 0 | 1:800 | 1:200 |
| Trypsin | 50 | 0 | 0 |
| Papain | 58 | 0 | 0 |

The results of these tests show that Wobenzym ® and its individual components pancreatin, bromelain, papain, lipase, amylase, trypsin and chymotrypsin are capable of stimulating the synthesis of TNF in mononuclear blood cells.

EXAMPLE 2

In order to quantify the synthetized TNF amount, the following tests were carried out:

$1 \times 10^6$/ml mononuclear cells from the blood of healthy donors were brought onto microtiter plates with 24 wells with Wobenzym ®, amylase, papain and bromelain (20 ug/ml). The supernatants were removed at different points in time after the beginning of incubation over a period of time of 24 hours and frozen at <20° C. until the TNF determination. The respective results of the TNF determination are represented in FIGS. 1b to e. The obtained individual results are summarized in a diagram in FIG. 1a, FIG. 2 shows the kinetics of the TNF synthesis in the first five hours after incubation with the respective inductive agent.

FIGS. 1a to e show the TNF concentration over a period of times of 24 hours. TNF can be detected for Wobenzym ® and its components over the entire test period. Especially high concentrations are achieved as compared with lipopolysaccharide if the enzymes amylase and bromelain are used.

Figure 2:
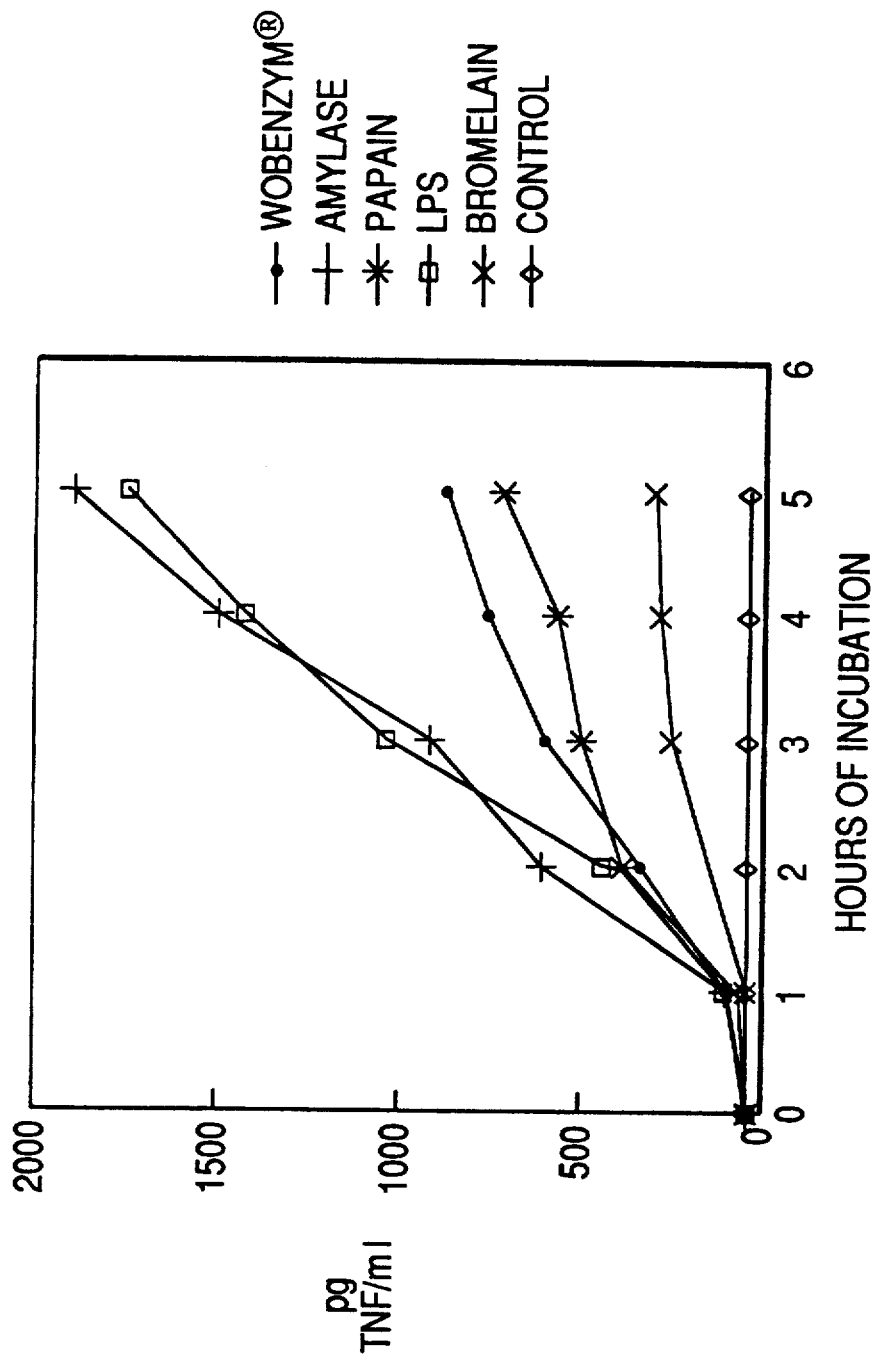
FIG. 2 is a graph showing the course of TNF concentration in the supernatants of mononuclear blood cells treated with Wobenzym ®, amylase, papain, LPS, bromelain, and a control over a 5 hour period.

FIG. 2 shows the course of the TNF concentration in the supernatants of mononuclear blood cells treated with enzyme over an incubation period of 5 hours. The highest TNF synthesis rates are obtained in the case of the induction with lipopolysaccharide and the enzyme amlyase, very good synthesis rates are obtained with Wobenzym and papain.

Figure 3A:
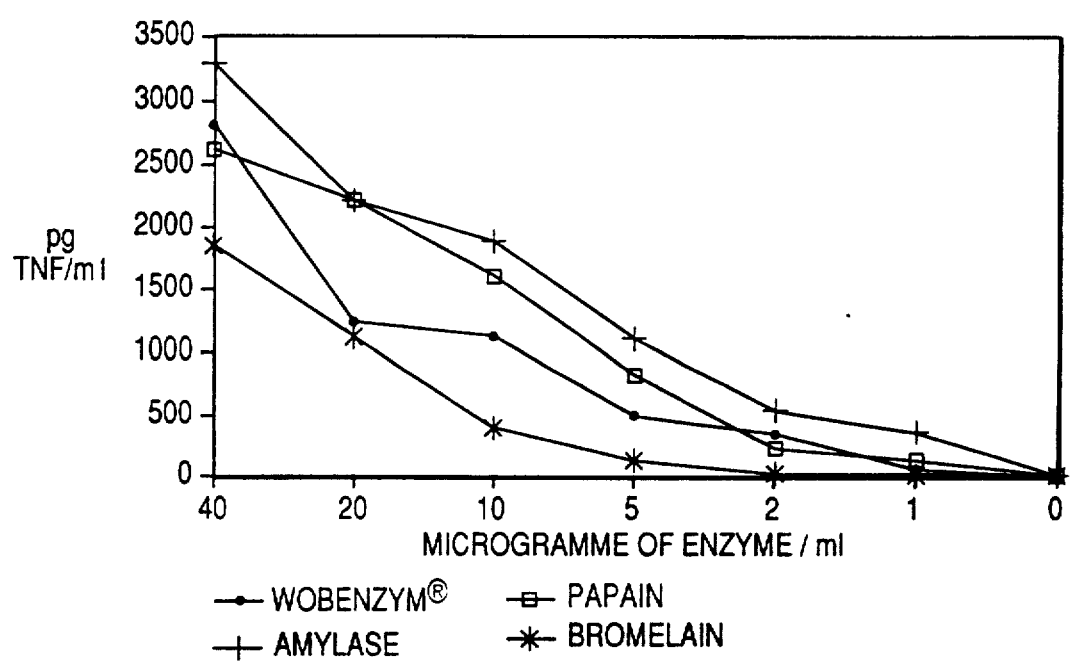
FIG. 3a is a graph summarizing TNF induction in mononuclear blood cells as a function of the concentration of enzyme (Wobenzym ®, amylase, bromelain, and papain) used for induction over a 7 hour period.
Figure 3B:
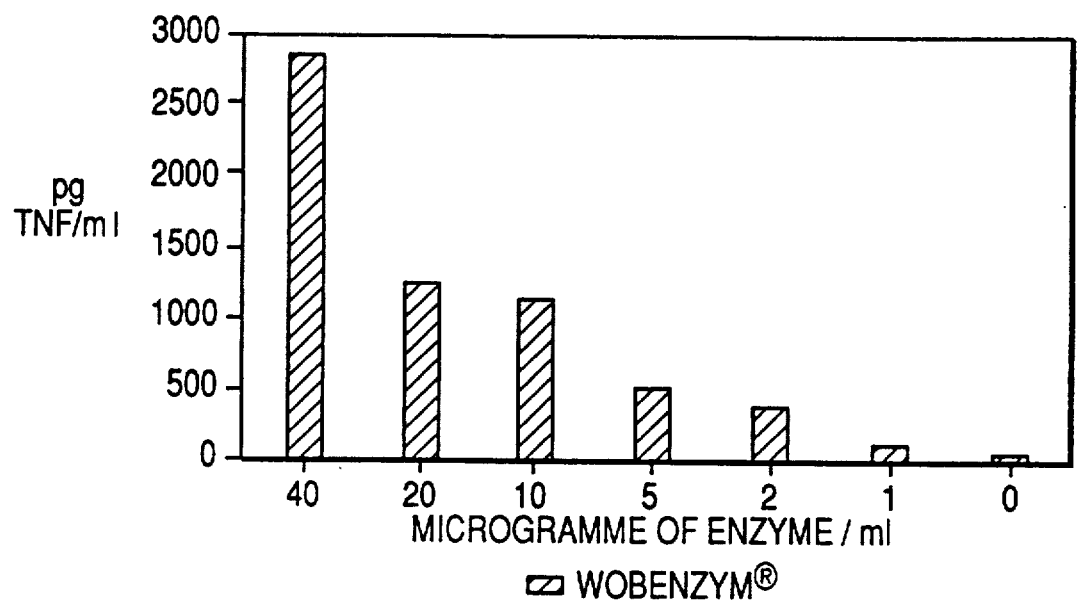
FIG. 3b is a graph showing TNF induction as a function of the concentration of Wobenzym ® used for induction over a 7 hour period.
Figure 3C:
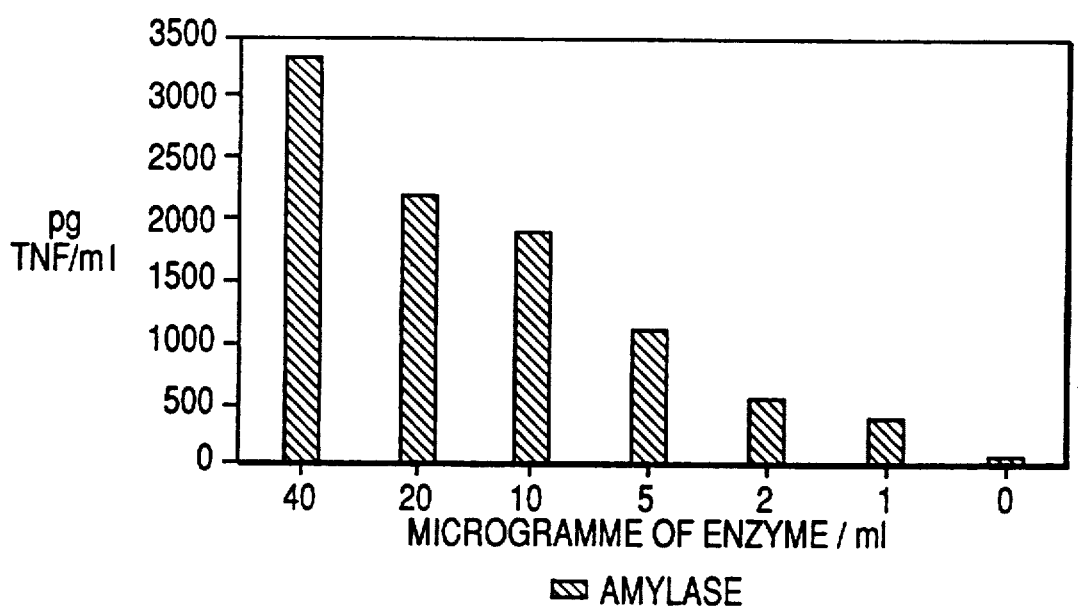
FIG. 3c is a graph showing TNF induction as a function of the concentration of amylase used for induction over a 7 hour period.
Figure 3D:
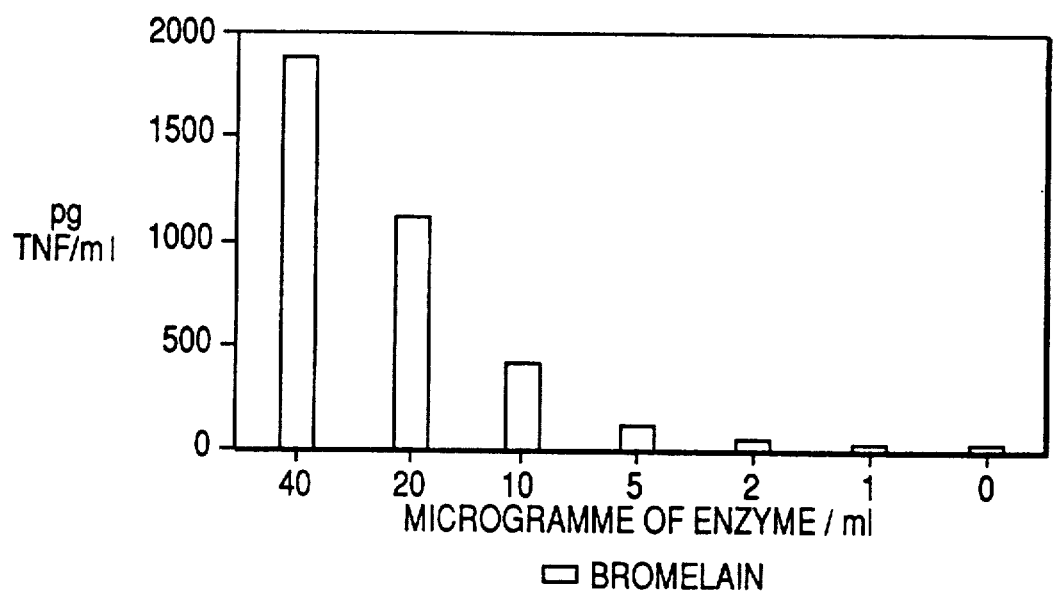
FIG. 3d is a graph showing TNF induction as a function of the concentration of bromelain used for induction over a 7 hour period.
Figure 3E:
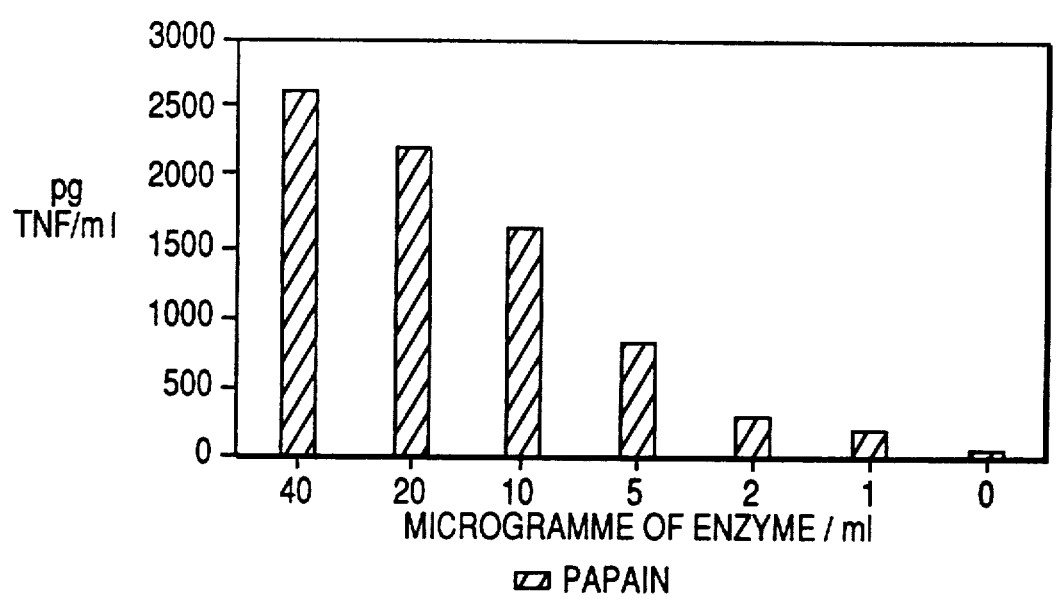
FIG. 3e is a graph showing TNF induction as a function of the concentration of papain used for induction over a 7 hour period.

The synthetized amount of TNF was furthermore determined as a function of the amount of enzyme used for induction. For this purpose, mononuclear cells from the blood of healthy donors of a concentration of $1 \times 10^6$/ml were incubated on microtiter plates with 24 wells in the presence of Wobenzym ®, amylase, bromelain or papain in the concentrations 40 µg, 20 µg, 10 µg, 5 µg, 2 µg or 1 µg per ml for 7 hours. The supernatants were frozen at −20° C. and subsequently used for TNF determination. The respective results are represented in FIGS. 3b to 3e. A summary of the obtained individual results is shown in FIG. 3a.

FIGS. 3a to e show that the formed amount of TNF increases with the concentration of the enzyme used for induction. The dependence of the induction on the concentration depends in turn of the respectively used enzyme or the enzyme concentration.

TNF DETERMINATION

L 929 (transformed mouse fibroblast line) in the growth phase (3rd to 4th day after transferring) were dissolved with trypsin and $5 \times 10^4$/well were applied onto 96-well microtiter plates. The supernatant was sucked off after 24 hours, 100 µl D (10 µg/ml) and 100 µl sample per well were used. After an incubation of further 24 hours the supernatant was again sucked off, living cells remaining adherent. These cells are coloured with crystal violet and the absorption was determined at 590 nm by means of a photometer. The percentage cytotoxicity results according to % cytotoxicity =

$$\frac{\text{absorption (control)} - \text{absorption (sample)}}{\text{absorption (control)}} \times 100$$

The determination of the TNF amount was carried out by means of a calibration curve which was made with rTNF (Genzym).

We claim:

1. A method for induction of the tumor necrosis factor, TNF, comprising incubating human mononucleocytes with a composition containing at least one enzyme selected from the group consisting of pancreatin, bromelain, papain, lipase, amylase, trypsin, and chymotrypsin.

2. The method of claim 1 wherein said lipase is triacyl glycerol lipase.

3. The method of claim 1 wherein said amylase is α-amylase.

4. The method of claim 1 wherein said composition comprises a combination of pancreatin, bromelain, papain, triacyl glycerol lipase, α-amylase, and at least one enzyme of the group consisting of trypsin and chymotrypsin.

5. The method of claim 1 wherein said composition additionally comprises rutoside.

6. The method of claim 4 wherein said composition additionally comprises rutoside.

7. The method of claim 1 wherein said composition comprises a mixture of about 50 to 200 mg of pancreatin, about 20 to 100 mg of bromelain, about 40 to 100 mg of papain, about 5 to 50 mg of triacyl glycerol lipase, about 5 to 50 mg of α-amylase, about 10 to 30 mg of trypsin, about 1 to 10 mg of chymotrypsin, and about 10 to 100 mg of rutoside $\times 3$ H$_2$O.

8. The method of claim 14 wherein said composition comprises a mixture of about 100 mg of pancreatin, about 45 mg of bromelain, about 60 mg of papain, about 10 mg of triacyl glycerol lipase, about 10 mg of a α-amylase, about 24 mg of trypsin, about 1 mg of chymotrypsin, and about 50 mg of rutoside $\times 3$ H$_2$O.

9. The method of claim 1 wherein said composition additionally comprises Serratia peptidase.

* * * * *

UNITED STATES PATENT AND TRADEMARK OFFICE
CERTIFICATE OF CORRECTION

PATENT NO. : 5,223,406
DATED : Jun. 29, 1993
INVENTOR(S) : Karl Ransberger; Gerhard Stauder It is certified that error appears in the above-indentified patent and that said Letters Patent is hereby corrected as shown below:

TITLE PAGE

[73] Assignee: delete "Emulsiongesellschaft" and insert --Emulsionsgesellschaft--.

[30] Foreign Application Priority Data: delete "8911862810" and insert --89118628.0--.

[56] References Cited: delete "Desser" and insert --Dresser--.

Col. 1, lines 53-68 and Col. 2, lines 1-25, Brief Description of Drawings should be moved to Col. 1, line 43, after "in viro." and prior to "The enzymes used".

Col. 3, line 62, delete "anti-TNF o" and insert --anti-TNF α--.

Col. 4, line 4, after "anti-TNF" insert --α--.

Col. 5, line 25, delete "<20°C." and insert -- -20°C--.

Col. 6, line 52, delete "14" and insert --7--.

Signed and Sealed this

Nineteenth Day of April, 1994

Attest:

BRUCE LEHMAN

Attesting Officer    Commissioner of Patents and Trademarks